(12) United States Patent
Msika et al.

(10) Patent No.: US 8,231,916 B2
(45) Date of Patent: Jul. 31, 2012

(54) USE OF A RICE PROTEIN HYDROLYSATE AS PIGMENTING ACTIVE PRINCIPLE

(75) Inventors: Philippe Msika, Versailles (FR); Dalale Naaïmi, Dijon (FR)

(73) Assignee: Laboratoires Expanscience, Courbevoie (FR)

( * ) Notice: Subject to any disclaimer, the term of this patent is extended or adjusted under 35 U.S.C. 154(b) by 335 days.

(21) Appl. No.: 12/299,009

(22) PCT Filed: Jul. 18, 2007

(86) PCT No.: PCT/EP2007/057441
§ 371 (c)(1), (2), (4) Date: Feb. 4, 2009

(87) PCT Pub. No.: WO2008/009709
PCT Pub. Date: Jan. 24, 2008

(65) Prior Publication Data
US 2009/0196837 A1    Aug. 6, 2009

(30) Foreign Application Priority Data
Jul. 18, 2006 (FR) ..................... 06 06780

(51) Int. Cl.
*A61K 36/89* (2006.01)
*A61K 36/00* (2006.01)
*A61K 38/00* (2006.01)
*A61Q 17/04* (2006.01)
*A01N 65/00* (2009.01)
*A61P 17/00* (2006.01)

(52) U.S. Cl. ......... 424/750; 424/59; 514/18.6; 514/18.8

(58) Field of Classification Search .................. None
See application file for complete search history.

(56) References Cited

U.S. PATENT DOCUMENTS

| 5,514,367 | A  | * | 5/1996  | Lentini et al. ................... 424/59 |
| 5,662,890 | A  |   | 9/1997  | Punto et al. |
| 6,231,837 | B1 | * | 5/2001  | Stroud et al. ..................... 424/59 |
| 2006/0141078 | A1 | * | 6/2006 | Guillou et al. ................ 424/750 |
| 2008/0305054 | A1 | * | 12/2008 | Vielhaber et al. ............... 424/59 |

FOREIGN PATENT DOCUMENTS

| EP | 0 575 452 B1 |   | 6/1998 |
| EP | 0 884 045 A1 |   | 12/1998 |
| EP | 1 656 970 A1 |   | 5/2006 |
| EP | 1 656 970 A1 |   | 5/2006 |
| FR | 2 553 285 A |   | 10/1984 |
| FR | 2 553 285 |   | 4/1985 |
| JP | 2002242256 | * | 1/2004 |
| WO | WO-96/22698 |   | 8/1996 |
| WO | WO 96/22698 |   | 8/1996 |
| WO | WO 02/102347 A2 |   | 12/2002 |
| WO | WO2008015341 | * | 2/2008 |

OTHER PUBLICATIONS

Webstie document entilted "Colorescience Wild to Mild Primer Sunreliable Skin Bronzer SPF 20", 1 page, downloaded from web on Apr. 20, 2011.*

* cited by examiner

*Primary Examiner* — Chris R Tate
*Assistant Examiner* — Russell Fiebig
(74) *Attorney, Agent, or Firm* — Foley & Lardner LLP

(57) ABSTRACT

The present invention concerns the use of a rice protein hydrolysate in order to pigment the skin and skin appendages. Thus, it is possible to intensify the normal pigmentation of the skin without sunlight. Preferred areas of applications are repigmentation of white patches of the skin, repigmentation of white patches of the skin as a consequence of pityriasis or due to the use of dermocorticoids; acceleration and intensification of the tanning process, stimulation of the constitutive photoprotection and improvement of the phototype, prevention of skin photocarcinogenesis. Advantageously, the rice protein hydrolysate comprises peptides of which at least 50% have a molecular mass in the range of between 300 and 3,500 Da.

12 Claims, No Drawings

USE OF A RICE PROTEIN HYDROLYSATE AS PIGMENTING ACTIVE PRINCIPLE

The present invention relates to the use of at least one rice protein hydrolysate, as a pigmenting active ingredient, in a dermatological, cosmetic or nutraceutical composition.

Melanin is a pigment that, in man, is responsible for the color of the skin, hair and eyes. Melanin is produced by melanocytes, cells found in the epidermis, from the amino acid tyrosine. Tyrosinase transforms tyrosine into DOPA and then DOPA-quinone. A number of enzymes then act to form melanin.

In the melanocyte, melanin is found in intracellular organelles (melanosomes). These melanosomes are transferred by melanocytes via arm-like structures (dendrites) toward nearby keratinocytes. The melanosome provides a protective function with respect to UV radiation by placing itself on top of the keratinocyte's nucleus, much like a parasol.

Melanocytes are located at the dermo-epidermal junction and fit between the keratinocytes of the basal layer. One melanocyte protects 36 keratinocytes; this is the so-called melanin unit.

In man, melanin is responsible for constitutive pigmentation and tanning. Via tanning, it protects skin cell DNA from the sun's ultraviolet (UV) rays (UVA and UVB). During extended exposure to the sun, the body tans because it manufactures more melanin, thus better protecting it from UV radiation. Melanin absorbs ultraviolet radiation by releasing in the form of heat the energy received. The definition of human phototypes integrates the concept of initial skin color and the capacity to tan and redden in the sun. Thus there is interest in shifting a given phototype to a higher phototype in order to provide greater photoprotection via a higher pigmentation ratio.

Because of over-exposure to the sun and/or genetic predisposition or skin disease, unsightly white spots, consistent with a loss of skin pigmentation, can appear. The most common skin affection of this type is the vitiligo.

White spots can also appear on the skin (primarily of tanned patients) in the case of Pityriasis versicolor, an affection due to the excessive proliferation of a fungus belonging to the *Malassezia* genus of yeasts. Today, it is known how to treat these yeasts. However, the treatment stops the infection but the white spots persist, normally until the next exposure to the sun. Likewise, hypochromia can appear after post-traumatic scarring or burns, concurrently with stretch marks or after the treatment of scaly dermatoses. To accelerate the disappearance of these white spots, a treatment supporting pigmentation can be advised.

White hairs (canities) appear when the hair bulbs stop producing melanin. The mechanism for this production stoppage remains poorly understood. On the other hand, the mechanism is known to be hereditary and related to age.

Today, people desire to have tan skin while limiting or eliminating exposure to UV radiation (natural or artificial) and while protecting the skin from early ageing and from other side effects of UV radiation.

The inventors have discovered, in a surprising and unexpected way, that rice protein hydrolysates (also called rice peptides) have the property of stimulating cutaneous pigmentation. Application of the active composition allows greater constitutive pigmentation and faster, more intense tanning during a shorter exposure. Consequently, the appearance of cutaneous ageing factors and other undesired effects due to UV radiation are slowed. Moreover, the patient reaches a higher phototype, which decreases the risks of cutaneous photocarcinogenesis.

Thus the first object of the invention is the use of a rice protein hydrolysate to produce a pigmenting, cosmetic, dermatological or nutraceutical composition for man and animals.

This composition stimulates cutaneous pigmentation (which can be constitutive or acquired) and thus can be used as a tanning accelerator.

The composition can be used in tanning booths either with a purely esthetic aim (tanning) or with a dermatological aim (strengthen the phototype of patients with light or sun-sensitive skin).

Thus, according to advantageous embodiments of the invention, the inventive composition increases and intensifies normal pigmentation of the skin without sunlight. It also accelerates and intensifies tanning. It can also stimulate constitutive photoprotection and strengthen phototype. It can also prevent photoageing. Finally, it can also prevent cutaneous photocarcinogenesis.

Within the scope of the present invention, "constitutive photoprotection" means phototype, i.e., the innate capacity to be protected from the sun by the sensitivity to reddening by UV radiation, the pigmentation genetically acquired without sun (normal complexion of the skin) and tanning following exposure (complexion of the skin after sunlight).

The invention also has as an object a method of cosmetic treatment to stimulate constitutive or acquired pigmentation, characterized in that a composition comprising at least one rice protein hydrolysate is applied by topical route. This method of cosmetic treatment notably accelerates the tanning and natural color of the skin without sunlight or allows tanning with little or no sunlight.

This composition can also be used to treat depigmentation (white) spots on the skin, such as vitiligo or iatrogenic hypopigmentation (dermal corticosteroids). The composition also can be used to re-pigment the skin of patients with pityriasis, in particular Pityriasis versicolor. It can also allow patients suffering from xeroderma pigmentosum to have sun-free stimulation of cutaneous pigmentation.

This composition can stimulate constitutive photoprotection and strengthen phototype.

The invention thus also has as an object the use of a rice protein hydrolysate to produce a composition or a drug to treat and to prevent depigmentation spots (re-pigment cutaneous white spots). Depigmentation spots can be due to or consecutive to an affection or a sensitization chosen among the group comprised of vitiligo, pityriasis (Pityriasis versicolor), use of dermal corticosteroids, scarring or intense exposure to the sun. Depigmentation spots can be due to significant photoageing.

The invention also has as an object the use of a rice protein hydrolysate to produce a capillary treatment to prevent and to treat white hair.

Finally, the invention has as an object the use of a rice protein hydrolysate to produce a composition or a drug to prevent cutaneous photocarcinogenesis.

Within the scope of the present invention, the expressions "rice protein hydrolysates" and "rice peptides" both indicate the product resulting from the enzymatic hydrolysis of rice proteins.

Rice peptides are already known in the prior art and processes for obtaining these peptides have already been described (EP 575452, WO 02/102347).

Rice protein hydrolysates are commercially available from SILAB under the name Nutriskin. These hydrolysates comprise low molecular weight peptides (less than 1,400 daltons). They can be obtained as described in international application WO 02/102347.

A method for preparing a rice protein hydrolysate comprises, for example, the following steps:
- solubilize rice proteins in water to obtain a suspension,
- hydrolyze this suspension in the presence of one or more proteases,
- advantageously filter on a membrane to eliminate the insoluble compounds, residual enzyme and high molecular weight peptides (greater than 10,000 daltons);
- and, optionally, perform a sterile filtration of the concentrate previously obtained.

The rice proteins used can be obtained by grinding rice grains (ex.: *Oryza sativa*). Rice protein concentrates are also available commercially (sold by Remy Industries, for example).

Advantageously, the method for preparing the rice protein hydrolysate does not include a fermentation or germination step. Moreover, the rice used in the inventive composition and/or implemented in the process above preferably belongs to the genus *Oryza* and more preferentially is the species *Oryza sativa* L. Advantageously, the rice hydrolysate used in the inventive composition, and that obtained in the method of preparation above, result from a rice fraction free of rice bran.

The rice protein hydrolysate used in the inventive method may comprise peptides having a mean molecular weight ranging from less than 300 daltons to more than 10,000 daltons, preferably a mean molecular weight between 300 daltons and 3,500 daltons.

In particular, preferably a rice protein hydrolysate comprising peptides having a molecular weight less than or equal to 10,000 daltons, preferentially a molecular weight less than or equal to 3,500 daltons, will be used. According to a particular embodiment of the invention, at least 75% by weight, advantageously at least 80% by weight, more advantageously at least 85% by weight of the peptides have a molecular weight between 300 Da and 3,500 Da. In particular, at least 50% by weight of the peptides, advantageously at least 55% in number of the peptides, have a molecular weight between 300 Da and 1,200 Da.

The concentration of rice peptides in the inventive composition (cosmetic, dermatological or nutraceutical) is advantageously between roughly 0.1% and roughly 20% by weight, more advantageously between roughly 1% and roughly 10% by weight, even more advantageously between roughly 4% and roughly 6% by weight, compared to the total weight of the composition.

The inventive composition can contain other active ingredients that pigment or color the skin (in addition to UV protection), leading to a complementary or synergistic effect.

Notably, the following can be cited as examples of pigmenting or coloring agents:
- agents that color the skin, such as dihydroxyacetone and melanins;
- agents that stimulate the natural pigmentation process, such as psoralens (8-methoxypsoralen, 5-methoxypsoralen, 4,5',8-trimethylpsoralen or vegetable extracts of *Psoralea corylifolia* and *Ammi majus*), carotenoids (lycopene, canthaxanthin), agents that stimulate the cyclic AMP pathway (1. cAMP analogs such as 8-bromo-cAMP or dibutyryl-cAMP, 2. forskolin, 3. isobutyl-methyl-xanthine or theophylline), of protein kinase C activators (diacylglycerols, in particular oleoylacetylglycerol), aliphatic or cyclic diols (1,2-propanediol, 5-norbornane-2,2-dimethanol, norbornane-2,2-dimethanol), monoterpene bicyclic diols, tyrosine derivatives (L-tyrosine, L-DOPA), dimethyl sulfoxide, lysosomotropic agents, thymidine dinucleotides, DNA fragments, melanocyte stimulating hormone analogs, 3-isobutyl-1-methylxanthine, nitric oxide donors (David A. Brown, Journal of photochemistry and photobiology B: biology 63 (2001) 148-161);
- vegetable extracts, in particular algae, exhibiting promelanogenic activity: *Laminaria digitata* (thalitan from CODIF).

Tyrosinase is an enzyme involved in melanogenesis. Thus, the inventive rice peptides can be combined with active ingredients able to:
- activate factors that induce tyrosinase synthesis;
- promote tyrosinase enzymatic activity;
- promote tyrosinase glycosylation (allow its absorption by melanosomes);
- increase overall melanocyte activity;
- promote the transfer of tyrosinase in premelanosomes;
- carrier melanin precursors;
- restrict cellular activity, thus preserving keratinocytes loaded with melanin.

Rice peptides can also be combined with oxidants or antioxidants, leading to a complementary or synergistic effect. As examples of antioxidants, the following can be cited: vitamin C, vitamin E, polyphenols (notably those extracted from green tea, grapes or pine), sulfur derivatives.

Rice peptides can also be associated with agents that protect cells from sunlight damage, other than antioxidants, acting on sun-scorched cells, p53, heat shock proteins, apoptosis, membrane lysis, cytokine release or cellular mediators.

According to another aspect of the invention, the inventive compositions also contain at least one UVB and/or UVA filter or sun block, such as the mineral and/or organic screens or filters known to those skilled in the art who will adapt the choices and concentrations according to the required degree of protection.

Moreover, the inventive compositions can contain exfoliants or hydrating agents such as alpha-hydroxy and salicylic acids and derivatives of same in ester form, for example.

The inventive compositions can also contain anti-inflammatory or soothing agents, agents that desensitize the skin such as NSAIDs (non-steroidal anti-inflammatory drugs), dermal corticosteroids, PPAR (peroxisome proliferator-activated receptor) agonists, licorice derivatives, bisabolol, isoflavones (of soy, for example) glycosylated or not, palmitoylethanolamide, unsaponifiables containing phytosterols and vitamin E, cyclooxygenase (COX) and/or lipoxidase (LOX) inhibitors, thermal spring water, sea water or water reconstituted from exogenous trace elements.

Lastly, the inventive compositions can also contain anti-ageing agents such as retinol, vitamins B3 C and A, lycopene, carotenes, carotenoids, alpha hydroxy acids (AHAs), beta hydroxy acids (BHAs), free, esterified or bound covalently, proteins of the extracellular matrix (glucosamine, chondroitin sulfate), collagen, elastin and their activators, furanic derivatives of avocado, phytosterols, unsaturated and polyunsaturated fatty acids, plant isoflavones (soy, clover), *lactobacillus* and other prebiotics and probiotics.

Within the scope of the treatment or prevention of white hair, the composition can in addition comprise hair growth activators (Minoxidil, Aminexil, etc.) or active ingredients that inhibit or slow hair loss. The compositions can also comprise hair perming agents and dyes, film-forming and setting agents and capillary hair treatments.

The inventive composition can be administered by topical or oral route.

Within the scope of topical application, the inventive composition comprises a dermatologically and/or cosmetically acceptable carrier, i.e., a carrier compatible with the skin. It can advantageously be provided in all the galenical forms normally used for topical application, in particular in the form of an aqueous, hydroalcoholic or oily solution, an oil-in-water, water-in-oil or multiple emulsion, an aqueous or oily gel, a liquid anhydrous product, paste or solid, a dispersion of oil in an aqueous phase using spheroids (nanospheres, nanocapsules, lipid vesicles), a transdermal device or in any other form for topical application.

This composition can be more or less fluid and have the appearance of a white or tinted cream, pomade, milk, lotion, serum, paste, foam or gel. It can optionally be applied to the skin in aerosol form. It can also be provided in solid form, for example in stick form. It can also be applied by means of a patch.

Within the scope of oral administration, the composition can be provided in the form of a capsule, hard gelatin capsule, tablet, granule, spray or oral solution. When the composition is provided in the form of a soft capsule or a hard gelatin capsule, the envelope of said soft capsules or said hard gelatin capsules can notably contain animal gelatin such as fish gelatin, glycerin, or a material of plant origin such as a starch or cellulose derivative, or a plant protein. When the composition is provided in the form of a hard gelatin capsule, tablet or granule, the active ingredients can be fixed on a powdery carrier such as silica, cellulose and maltodextrin.

The inventive composition can also contain typical additives used in the field of cosmetics, such as stabilizers, preservatives, antioxidants, solvents, fragrances, chelating agents, odor absorbers, chemical or mineral filters, mineral pigments, surfactants, polymers, silicone oils and dyes or exfoliants.

The aim of the following examples is to evaluate the effects of a rice peptide-based active ingredient on pigmentation and cutaneous photoprotection.

Pigmentation: multi-parametric evaluation of the following effects:
  Effect on melanin production by normal human melanocytes co-cultured with irradiated or non-irradiated keratinocytes (NHEM-NHEK) (example 2)
  Effect on tyrosinase activity in melanocyte (NHEM) cultures (example 3)
  Effect on dendrite formation in melanocytes co-cultured with keratinocytes (NHEM-NHEK) (example 4)
  Effect on melanosome transfer by melanocytes to neighboring keratinocytes (example 5)
  Effect on the pigmentation of living skin (example 6)
Photoprotection:
  Effect on glutathione (GSH) synthesis by human cutaneous fibroblasts irradiated with UVA (example 7)

EXAMPLE 1

Inventive Rice Peptides

Rice peptides are obtained by enzymatic hydrolysis of rice proteins. The residual proteins are eliminated by ultrafiltration with a cutoff threshold of 10,000 Da. The peptides are concentrated by evaporation of water under vacuum or by nanofiltration (200 Da) to 5% dry matter. The dry matter can be obtained by dry evaporation, lyophilization or atomization.

The characteristics of the rice peptides obtained are summarized in table 1 below:

TABLE 1

| Rice peptide characteristics | |
|---|---|
| Degree of hydrolysis | 30%-40% |
| % dry matter (DM) | 4-6% or >80% if atomized |
| pH | 4-7 |
| Proteins/DM | 80%-95% |
| Alpha amino nitrogen/DM | 15%-25% |
| Free amino acids | <4% |
| Sulfur amino acids | <3% |
| Distribution by molecular weight | >3,500 Da: <2% |
| | 3,500-1,200 Da: 20-35% |
| | 1,200-300 Da: 50-65% |
| | <300 Da: 5-15% |

These rice peptides are then tested in examples 2 to 7 below.

EXAMPLE 2

Measuring the Melanin Produced by Normal Human Melanocytes Co-Cultured with Irradiated or Non-Irradiated Keratinocytes (NHEM/NHEK)

NHEM/NHEK co-cultures were inoculated in 24-well plates. Three series of identical plates were prepared in order to evaluate:
  a. Melanin quantity by spectrophotometry;
  b. Cell viability at the end of the experiment (MTT test);
  c. Protein quantity.

After 24 hours of incubation at 37° C., the culture medium was discarded and replaced by a medium containing or not containing (control) rice peptides (at 0.1, 0.5 and 2 mg/ml) or the pro-pigmenting reference molecule (IBMX=isobutylmethylxanthine at 200 μM) and then the co-cultures were incubated at 37° C. for 10 days.

One batch of plates was not irradiated (batch NHEM/NHEK non-irradiated co-culture).

The second batch was irradiated for four consecutive days at a dose of 25 mJ/cm$^2$ UVB plus 300 mJ/cm$^2$ UVA and then the culture medium containing or not containing the products (rice peptides or IBMX) was changed. The co-cultures were then cultivated for 72 h without irradiation and then irradiated again with 25 mJ/cm$^2$ UVB plus 300 mJ/cm$^2$ UVA for four consecutive days (with a change of medium after 48 h).

At the end of the treatment, the culture medium was discarded and the melanin contained in the cells was extracted by a 0.5 N NaOH solution, and then the quantity of melanin produced under each co-culture condition was evaluated by measuring the optical density of the samples at 405 nm against a range of exogenous melanin.

Cell Viability and Protein Quantity

The results of the MTT test are presented in table 2 below:

TABLE 2

| Evaluation of cell viability in NHEM/NHEK co-cultures | | |
|---|---|---|
| Sample | % viability in non-irradiated co-cultures | % viability in irradiated co-cultures |
| Control | 100 | 100 |
| 200 μM IBMX | 118 | 111 |
| 0.1 mg/ml rice peptides | 122 | 112 |
| 0.5 mg/ml rice peptides | 131 | 122 |
| 2.0 mg/ml rice peptides | 138 | 126 |

Proteins concentration results are presented in table 3 below:

TABLE 3

Protein concentrations in co-cultures

| Sample | Proteins (mg/ml) in non-irradiated co-cultures | Proteins (mg/ml) in irradiated co-cultures |
|---|---|---|
| Control | 0.828 | 0.767 |
| 200 µM IBMX | 0.933 | 0.833 |
| 0.1 mg/ml rice peptides | 0.864 | 0.742 |
| 0.5 mg/ml rice peptides | 0.890 | 0.774 |
| 2.0 mg/ml rice peptides | 0.942 | 0.973 |

Rice peptides do not exhibit any toxicity on NHEM/NHEK co-cultures (same remark for IBMX). On the contrary, an increase in cell protein quantity and metabolic activity in the presence of rice peptides and IBMX were demonstrated.

Measuring Melanin

The results are presented in table 4 below:

TABLE 4

Modulation of melanin production in NHEM/NHEK co-cultures

| Sample | % increase in melanin quantity compared to the control in non-irradiated co-cultures | % increase in melanin quantity compared to the control in irradiated co-cultures |
|---|---|---|
| 200 µM IBMX | +18%* | +14%* |
| 0.1 mg/ml rice peptides | +15%* | +7%$ |
| 0.5 mg/ml rice peptides | +12%* | +5% |
| 2.0 mg/ml rice peptides | +29%* | +11%* |

*Statistically different from the control ($p < 0.01$, Dunnett's test)
$Statistically different from the control ($p < 0.05$; Dunnett's test)

Under non-irradiated conditions, the rice peptides tested at concentrations of 0.1, 0.5 and 2.0 mg/ml significantly increased melanin quantity (by +15%, +12% and +29%, respectively, compared to the control; $p<0.01$).

Under irradiated conditions, the rice peptides tested at 2 mg/ml significantly increased melanin quantity (+11% compared to the control; $p<0.01$). At 0.5 mg/ml and 0.1 mg/ml, this stimulation was less marked.

The rice peptides act on melanin synthesis in the same way as the pro-pigmenting reference molecule (IBMX).

Moreover, as for IBMX, stimulation of melanin synthesis by rice peptides correlates with an increase in cell protein quantity and metabolic activity (% viability) (see tables 2 and 3).

EXAMPLE 3

Effect on Tyrosinase Activity in Melanocyte Cultures (NHEM)

Melanocytes (NHEM) were pre-cultivated in 96-well plates for 24 hours, and then the cells were treated with rice peptides or IBMX (200 µM) for 72 hours at 37° C.

At the end of the treatment, the tyrosinase contained in the cells was extracted and the oxidation reaction of L-DOPA to DOPA-quinone was monitored for 1 hour at 37° C. after adding L-DOPA (the reaction substrate). Tyrosinase activity was then evaluated by measuring the optical density of the samples at 450 nm against a standard range of tyrosinase.

The results are presented in table 5 below:

TABLE 5

Effect of treatments on tyrosinase activity of human melanocytes

| Sample | Tyrosinase activity (units/ml) | % increase compared to the control |
|---|---|---|
| Control | 29.12 | — |
| 200 µM IBMX | 60.88* | +109% |
| 0.5 mg/ml rice peptides | 46.29* | +59% |
| 2.0 mg/ml rice peptides | 79.18* | +172% |

*Statistically different from the control ($p < 0.01$, Dunnett's test)

The rice peptides, tested at 0.5 mg/ml and 2 mg/ml, significantly stimulated the tyrosinase activity of human melanocytes in a dose-dependant fashion (+59% and +172%, respectively, compared to the control; $p<0.01$).

EXAMPLE 4

Evaluation of Dendrite Formation of Melanocytes in Co-Culture with Keratinocytes (NHEM/NHEK)

NHEM/NHEK co-cultures were inoculated 24 hours before the test in 96-well plates and then were incubated for 72 hours in the presence or absence (control) of rice peptides (at 0.1, 0.5 and 2.0 mg/ml) or IBMX (at 200 µM).

Dendrite formation was demonstrated by fluorescent labeling using an anti-MeI-5 antibody (TRP-1, tyrosinase related protein 1) specific to melanosomes. Labeling was revealed by a secondary antibody, GAM-FITC.

This analysis made it possible to determine the density of melanocyte extensions (number and total length of dendrites per melanocyte).

Effect on Dendrite Formation of Melanocytes in Co-Culture with Keratinocytes

TABLE 6

Measurement of dendrite formation of melanocytes in NHEM/NHEK co-culture: Analysis of dendrite number per melanocyte.

| Treatment | Mean number of dendrites per melanocyte | % increase compared to the control |
|---|---|---|
| Control | 12.18 | — |
| 200 µM IBMX | 15.30* | +26% |
| 0.1 mg/ml rice peptides | 12.73 | +4% |
| 0.5 mg/ml rice peptides | 14.52* | +19% |
| 2.0 mg/ml rice peptides | 15.43* | +27% |

*Statistically different from the control ($p < 0.01$, Dunnett's test)

TABLE 7

Measurement of dendrite formation of melanocytes in NHEM/NHEK co-culture: Analysis of dendrite length.

| Treatment | Mean dendrite length per melanocyte | % increase compared to the control |
|---|---|---|
| Control | 228.18 | — |
| 200 µM IBMX | 402.50$ | +76% |

TABLE 7-continued

Measurement of dendrite formation of melanocytes in NHEM/NHEK co-culture: Analysis of dendrite length.

| Treatment | Mean dendrite length per melanocyte | % increase compared to the control |
| --- | --- | --- |
| 0.1 mg/ml rice peptides | 276.09 | +21% |
| 0.5 mg/ml rice peptides | 285.20 | +25% |
| 2.0 mg/ml rice peptides | 381.82* | +67% |

*$Statistically different from the control (* $p < 0.01$, $ $p < 0.05$, Dunnett's test)

The rice peptides tested at 2 mg/ml and 0.5 mg/ml increased in a dose-dependant fashion the number and length of melanocyte extensions. At 0.1 mg/ml the effect on dendrite number is not visible although a small effect on length is still observed.

EXAMPLE 5

Effect on Melanosome Transfer by Melanocytes to Neighboring Keratinocytes

Protocol:

Before inoculation, the melanocytes were "loaded" with the fluorescent probe for tracing melanosome transfer carboxyfluorescein diacetate succinimidyl ester (CFDA).

The "loaded" melanocytes were then incubated in co-culture with keratinocytes at 37° C. (NHEM/NHEK). Several analyses were performed in order to adjust the parameters for acquisition by flow cytometry:

"Non-loaded" NHEM/NHEK co-culture.

NHEK cultures alone.

"Loaded" or "non-loaded" NHEM cultures, tested alone.

At 60-80% confluence, the culture medium was replaced by a medium containing or not containing (control) rice peptides (0.5 and 2 mg/ml) or IBMX, and then the cells were cultivated at 37° C. After 72 h of incubation, the cells were again treated as before and then incubated for 72 h at 37° C. Each treatment condition was carried out in triplicate.

At the end of the treatment, the cells were trypsinated, fixed, permeabilized and then labeled with an anti-cytokeratin antibody (specific to keratinocytes). Labeling was revealed using a secondary antibody directed against the anti-cytokeratin antibody and coupled with phycoerythrin. The fluorescence parameters were measured by flow cytometry.

Analysis of Results by Flow Cytometry:

The cytometric analysis was parameterized (using the various analyses performed) in order to select in the total cellular population (NHEM/NHEK) only the positive keratinocytes, i.e., those keratinocytes having incorporated the fluorescent CFDA probe (indicating melanosome transfer) and exhibiting anti-cytokeratin labeling (specific to keratinocytes). This population of "doubly labeled" keratinocytes is obligatorily the result of melanosome transfer from melanocyte to keratinocyte.

Results and Conclusions:

The results are presented in table 8 below:

TABLE 8

Effect of treatments on melanosome transfer from melanocytes to keratinocytes

| Sample | Mean % of positive cells (CFDA/cytokeratin double labeling) | % increase compared to the control |
| --- | --- | --- |
| Control | 18.1 | — |
| 200 µM IBMX | 26.7* | +48% |
| 0.5 mg/ml rice peptides | 23.3* | +29% |
| 2.0 mg/ml rice peptides | 23.1* | +28% |

*$Statistically different from the control (* $p < 0.01$, $ $p < 0.05$, Dunnett's test)

The rice peptides tested at 0.5 mg/ml and 2 mg/ml induced a significant increase in melanosome transfer (29% and 28%, respectively, compared to the control). The rice peptides thus exhibit a stimulating effect on melanosome transfer.

EXAMPLE 6

Effect on Pigmentation of Living Skin

Skin samples obtained from a mammary biopsy were treated by topical application of rice peptides (at 0.1, 0.5 and 2.0 mg/ml) or IBMX (at 200 µM) (application of 20 µl, or roughly 5 Mg/cm$^2$). The explants were then maintained for 144 hours at 37° C.

The treated and control areas were photographed at the end of treatment and skin coloration was analyzed visually.

IBMX slightly increased skin pigmentation after 144 hours of culture.

The rice peptides increased in a dose-dependant fashion the pigmentation of the skin after 144 h of culture. The active ingredient exhibits a pro-pigmenting effect consistent with the results obtained in the other tests performed.

Conclusion from Examples 2 to 6

The examples previously cited demonstrate a pro-pigmenting effect of rice peptides. Indeed, it was shown that rice peptides increase the synthesis of melanin in irradiated or non-irradiated NHEM/NHEK co-cultures; increase tyrosinase activity (key enzyme in melanogenesis); increase the number and length of melanocyte extensions; increase the transfer of melanosomes from melanocytes to keratinocytes and increase the pigmentation of skin explants.

Moreover, the activity of rice peptides in the various studies performed is comparable to the activity of IBMX, used here as a reference pro-pigmenting molecule.

The rice peptide-based active ingredient is thus a tanning accelerator. Indeed, with or without exposure to UV light, it induces a strong stimulation of cutaneous pigmentation.

EXAMPLE 7

Effect on Glutathione (GSH) Synthesis in Human Cutaneous Fibroblasts Irradiated with UVA Dermal fibroblasts were inoculated in 60 mm petri dishes. The cells were pre-treated for 18 hours with 5 mM rice peptides or N-acetyl-cysteine (NAC=reference antioxidant molecule) and then irradiated at a dose of 15 J/cm² UVA. After irradiation, the fibroblasts were incubated for an additional 3 h at 37° C.

At the end of the treatment, two series of samples were collected in order to evaluate:
a. Total quantity of proteins according to the Lowry method.
b. The ratio of intracellular glutathione by assay (commercial kit).

The results are presented in table 9 below:

TABLE 9

Modulation of intracellular glutathione in dermal fibroblasts irradiated with UVA.

|  | GSH (μM) | Total proteins (g/l) | GSH (μmol/g proteins) | % increase compared to irradiated control cells |
|---|---|---|---|---|
| Control cells | 18.30 | 0.764 | 23.95 | — |
| Control cells + 15 J/cm² UVA | 15.50 | 0.708 | 21.89 | −8.60% vs. control cells |
| NAC (5 mM) | 21.10 | 0.748 | 28.209 | 29 |
| 0.5% DM rice peptides | 17.70 | 0.718 | 24.65 | 13 |
| 1% DM rice peptides | 18.70 | 0.714 | 26.19 | 20 |
| 1.5% DM rice peptides | 21.20 | 0.753 | 28.15 | 29 |

Irradiation at a dose of 15 J/cm² decreases by almost 9% the intracellular GSH ratio in fibroblasts compared to non-irradiated cells.

NAC, at a concentration of 5 mM, increases by 29% the GSH ratio in irradiated cells.

Rice peptides at concentrations of 0.5%-1.0% DM and 1.5% DM increase by 13%, 20% and 29%, respectively, the GSH ratio in fibroblasts subjected to UVA stress.

In other words, rice peptides are able to compensate for the decrease in intracellular GSH ratios following UVA irradiation.

General Conclusion:
Rice peptides stimulate tanning while protecting the skin from the harmful effects of the sun.

EXAMPLE 8

Formulations

8a - Face cream

|  | % |
|---|---|
| Isononyl isononanoate | 6.000 |
| Di-C$_{12-13}$ alkyl malate | 3.000 |
| Isocetyl stearate | 4.000 |
| Butylene glycol | 1.000 |
| Rice peptides | 3.000 |
| Dicaprylyl ether | 5.000 |

8a - Face cream (continued)

|  | % |
|---|---|
| Silanediol salicylate | 1.000 |
| Arachidyl alcohol | 1.650 |
| Tromethamine | 1.180 |
| Cetyl alcohol | 0.5 |
| Salicylic acid | 1.000 |
| Ascorbyl glucoside | 1.000 |
| Glycine | 1.000 |
| Tocopheryl acetate | 1.000 |
| Behenylic alcohol | 0.900 |
| Squalane | 0.790 |
| Sodium citrate | 0.660 |
| PPG-12/SMDI copolymer | 0.100 |
| Arachidyl glucoside | 0.350 |
| Fragrance | 0.400 |
| *Sclerotium* gum | 0.300 |
| Cetearyl alcohol | 0.430 |
| Citric acid | 0.110 |
| Sepigel 305* | 0.100 |
| Preservative system | QS |
| Water | QSP 100 |

*product sold by Seppic

8b - Anti-ageing sun and tanning cosmetic (Quantity: 100 g)

|  | % |
|---|---|
| Water | 64.83 |
| Rice peptides | 7 |
| Furanic unsaponifiable of avocado | 2 |
| Butylene glycol | 3 |
| Cetyl alcohol | 6 |
| C$_{12-13}$ Alkyl lactate | 2 |
| Mineral oil | 7 |
| Ceteth-20 | 2 |
| Stearic acid | 1 |
| Cinnamate | 5 |
| Mexoryl SX | 3 |
| Mexoryl XL | 4 |
| Ultrafine titanium dioxide | 7 |
| Zinc oxide | 2 |
| Tinosorb M and S | 4 |
| Tocopherol acetate | 0.50 |
| Propylene glycol | 0.56 |
| Disodium EDTA | 0.52 |
| Triethanolamine | 0.80 |
| Preservative | 0.30 |
| Citric acid | 0.25 |
| Methyl paraben | 0.11 |
| Steareth-20 | 1 |
| Sodium metabisulfite | 0.05 |
| Sodium sulfite | 0.05 |
| Propyl paraben | 0.03 |

8c - Anti white spot roll-on (Quantity: 100 g)

|  | % |
|---|---|
| Petrolatum | 6.00 |
| Hydrogenated palm oil | 4.00 |
| Glycerol caprylo caprate | 2.00 |
| Sucrose ester 7 (Sucrose distearate) | 6.00 |
| Squalane | 1.00 |
| *Candelilla* wax | 2.00 |
| Sucrose ester 11 (Sucrose stearate) | 0.50 |
| Rice peptides | 2.00 |
| Sunflower concentrate | 2.00 |

8c - Anti white spot roll-on (Quantity: 100 g)

|  | % |
|---|---|
| Glycerol | 5.00 |
| Glucodextrin | 1.00 |
| Trometamine | 0.01 |
| Xanthan gum | 0.20 |
| Hydroxymethylglycinate A | 0.60 |
| Citric acid | 0.32 |
| Cyclomethiconol | 5.00 |
| Ceramide/Cholesterol | 0.60 |
| Purified water | 5.00 |

8d - Summer tan maintenance cream (Quantity: 100 g)

|  | % |
|---|---|
| Squalane | 1.00 |
| Erythrityl ester | 4.00 |
| Decyl pentanoate | 4.00 |
| Cetearyl glucoside | 2.00 |
| Lauryl ether 23 OE | 1.00 |
| Cutina CBSV | 1.00 |
| Beeswax | 0.50 |
| Myristyl myristate | 1.00 |
| Preservative | 0.30 |
| Thick petrolatum | 5.00 |
| Squalane gel | 3.00 |
| Rice peptides | 5.00 |
| Purified water | 56.51 |
| Phenoxyethanol | 0.80 |
| Sodium EDTA | 0.10 |
| Citric acid | 0.14 |
| Potassium sorbate | 0.45 |
| Glycerin | 5.00 |
| Thickener | 0.50 |
| Soda lye | 0.30 |
| 60° Polyacrylamide gel | 1.00 |
| 35° Vitamin E acetate | 0.50 |
| Fragrance | 0.50 |
| Lupine peptide | 1.00 |
| Cyclomethyconol | 7.00 |
| TIO2 silica | 1.00 |
| 85% Genistein | 0.10 |
| PEG 300 | 0.90 |

8e - Tanning cream for vitiligo and hypopigmentation (Quantity: 100 g)

|  | % |
|---|---|
| Montanov 68 | 3 |
| Amphisol K | 0.50 |
| Miglyol 812 | 6 |
| Preservative | 0.30 |
| Shea butter | 1 |
| Rice peptides | 1 |
| Polyphenol | 0.5 |
| DHA | 2 |
| Na$_2$ EDTA | 0.10 |
| Citric acid | 0.01 |
| Preservative | 0.40 |
| Butylene glycol | 1 |
| Gelling agent | 0.25 |
| Soda lye | 0.4 |
| Manganese gluconate | 0.05 |
| Zinc salt | 0.10 |
| Purified water | QSP |

8f - Self-tanning and fortifying capillary nutraceutical soft capsule

|  | % |
|---|---|
| Cysteine or sulfur amino acid derivatives | 0.100 |
| Rice peptides | 500 |
| Group B vitamin | 1 |
| Pea hydrolysates | 50 |
| Duck feather hydrolysates | 50 |
| Excipient | QS |

8g - Treatment of hypopigmentation by oral route

|  | % |
|---|---|
| Mucilage (sodium alginate) | 500 mg |
| Fish oil | 500 mg |
| Rice peptides | 100 mg |
| Zinc salt | 1 mg |
| Carrot extract | 325 mg |
| Lycopene | 50 mg |
| Soft capsule excipient | QS |

8h - No-sun anti-ageing and tanning cream gel (Quantity: 100 g)

|  | % |
|---|---|
| Carbopol Etd 2020 | 0.6 |
| Xanthan gum | 0.15 |
| 85% Genistein | 0.1 |
| Retinol | 0.5 |
| NaOH | 0.001 |
| Preservative | 0.9 |
| Rice peptides | 2 |
| Glucodextrin | 2 |
| Fragrance | 0.7 |
| Silicone | 0.3 |
| Purified water | QSP |

8i - Pigmenting wipes (Quantity: 100 g)

|  | % |
|---|---|
| Poloxamer 184 | 1.0000 |
| Fragrance | 0.2000 |
| Purified water | 91.1550 |
| PEG-32 | 4.0000 |
| Preservative | 1.0000 |
| Chlorhexidine | 0.1500 |
| Phenoxyethanol | 0.1000 |
| Allantoine | 0.2000 |
| Rice peptides | 5.0000 |
| Solubilizer | 1.0000 |
| Trometamine | 0.1950 |

| 8j - Hydro-glyco-alcohol solution for growing and coloring the hair | |
| --- | --- |
| | % |
| Denatured alcohol | 70% |
| Cyclodextrin | 2% |
| Glycol | 25% |
| Aminexil | 1% |
| Minoxidil | 0.3% |
| Water | QSP 100% |

The invention claimed is:

1. A method for pigmenting, hyperpigmenting or repigmenting the skin and skin structure of a subject in need thereof comprising topically applying to the subject a composition comprising 3% to 20% by weight of rice protein hydrolysate compared to the total weight of the composition.

2. The method of claim 1, for increasing and intensifying normal pigmentation of the skin without sunlight, accelerating and intensifying tanning, stimulating constitutive photoprotection and strengthening the phototype, delaying the onset of the appearance of cutaneous photocarcinogenesis and delaying the onset of the appearance of photoageing.

3. The method of claim 1, for re-pigmenting cutaneous white spots.

4. The method of claim 1, for re-pigmenting cutaneous white spots consecutive to an affection or sensitization chosen among the group comprised of vitiligo, pityriasis, use of dermal corticosteroids, scarring or intense exposure to the sun.

5. The method of claim 1, wherein the composition is a hair care product to treat white hair and to delay the onset of its appearance.

6. The method of claim 1, wherein the rice protein hydrolysate comprises peptides of which at least 50% have a molecular weight between 300 and 10,000 Da.

7. The method of claim 1, wherein the rice protein hydrolysate comprises peptides of which at least 50% have a molecular weight between 300 and 3 500 Da.

8. The method of claim 6, wherein at least 50% of the peptides have a molecular weight between 300 and 1,200 Da.

9. The method of claim 1, wherein the composition comprises in addition antioxidants, photoprotectors, hydrating agents, dyes, hyper-pigmenting agents or anti-ageing agents.

10. A method for stimulating constitutive or acquired pigmentation in a subject in need thereof, comprising topically applying to the subject a composition comprising 3% to 20% by weight of at least one rice protein hydrolysate compared to the total weight of the composition.

11. The method according to claim 10, for accelerating the tanning and the natural color of the skin without sunlight.

12. The method according to claim 1, wherein the composition comprises 4% to 20% by weight of a rice protein hydrolysate compared to the total weight of the composition.

\* \* \* \* \*